(12) United States Patent
Ohba et al.

(10) Patent No.: US 7,191,109 B2
(45) Date of Patent: Mar. 13, 2007

(54) POSITRON EMISSION TOMOGRAPH APPARATUS

(75) Inventors: Hiroyuki Ohba, Hamamatsu (JP); Hideo Tsukada, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 753 days.

(21) Appl. No.: 10/203,161

(22) PCT Filed: Jan. 29, 2001

(86) PCT No.: PCT/JP01/00579

§ 371 (c)(1),
(2), (4) Date: Aug. 6, 2002

(87) PCT Pub. No.: WO01/59477

PCT Pub. Date: Aug. 16, 2001

(65) Prior Publication Data

US 2003/0014132 A1    Jan. 16, 2003

(30) Foreign Application Priority Data

Feb. 7, 2000    (JP)    ............................. 2000-029238

(51) Int. Cl.
  *G06G 7/48*    (2006.01)
  *G06G 7/58*    (2006.01)
  *A61K 49/04*   (2006.01)
(52) U.S. Cl. ............................. 703/6; 703/11; 424/9.4
(58) Field of Classification Search .................... 703/6, 703/11; 424/1.11, 9.4
  See application file for complete search history.

(56) References Cited

U.S. PATENT DOCUMENTS 4,150,292 A    4/1979    Ter-Pogossian ............. 250/363

(Continued)

FOREIGN PATENT DOCUMENTS

JP    4-138394    5/1992

(Continued)

OTHER PUBLICATIONS

Lee et al.; "Robust extraction of input function from H(2)(15)O dynamic myocardial positron emission tomography using independent component analysis"; IEEE Conf. Record, Nuc. Sci. Symp.; pp. 990-994, Oct. 1999.*

(Continued)

*Primary Examiner*—Hugh Jones
(74) *Attorney, Agent, or Firm*—Drinker Biddle & Reath LLP

(57) ABSTRACT

In a PET apparatus 1, in a calculation processing unit 50, for each frame, radiation data for a region of interest K of a measurement-subjected part H is extracted, and then the optimum administration rate of a labeled substance T is calculated based on the radiation data such that the radiation concentration for the region of interest K will be steady regardless of the physiological state (blood flow rate etc.) of the subject S. In an administration rate control unit 60, feedback control of the administration rate of the labeled substance into the subject S is carried out based on the calculated optimum administration condition. As a result, the change in the amount accumulated of the labeled substance T in the region of interest K between before and after administration of a drug being tested Y can be obtained easily and precisely in real time as the amount of change in the radiation concentration, and it becomes possible to grasp the measurement results rapidly and easily.

6 Claims, 10 Drawing Sheets

U.S. PATENT DOCUMENTS

| | | | | |
|---|---|---|---|---|
| 4,409,966 A | 10/1983 | Lambrecht et al. | ........... | 128/1.1 |
| 5,027,817 A | 7/1991 | John | ........................ | 128/653 |
| 5,687,208 A | 11/1997 | Bae et al. | ...................... | 378/8 |
| 5,924,987 A * | 7/1999 | Meaney et al. | ............. | 600/420 |

FOREIGN PATENT DOCUMENTS

JP 5-249245 9/1993

OTHER PUBLICATIONS

J.R. Votaw, "Signal-to-Noise Ratio in Neuro Activation Pet Studies," IEEE Transactions on Medical Imaging, vol. 15, No. 2, Apr. 1996, pp. 197-205.

* cited by examiner

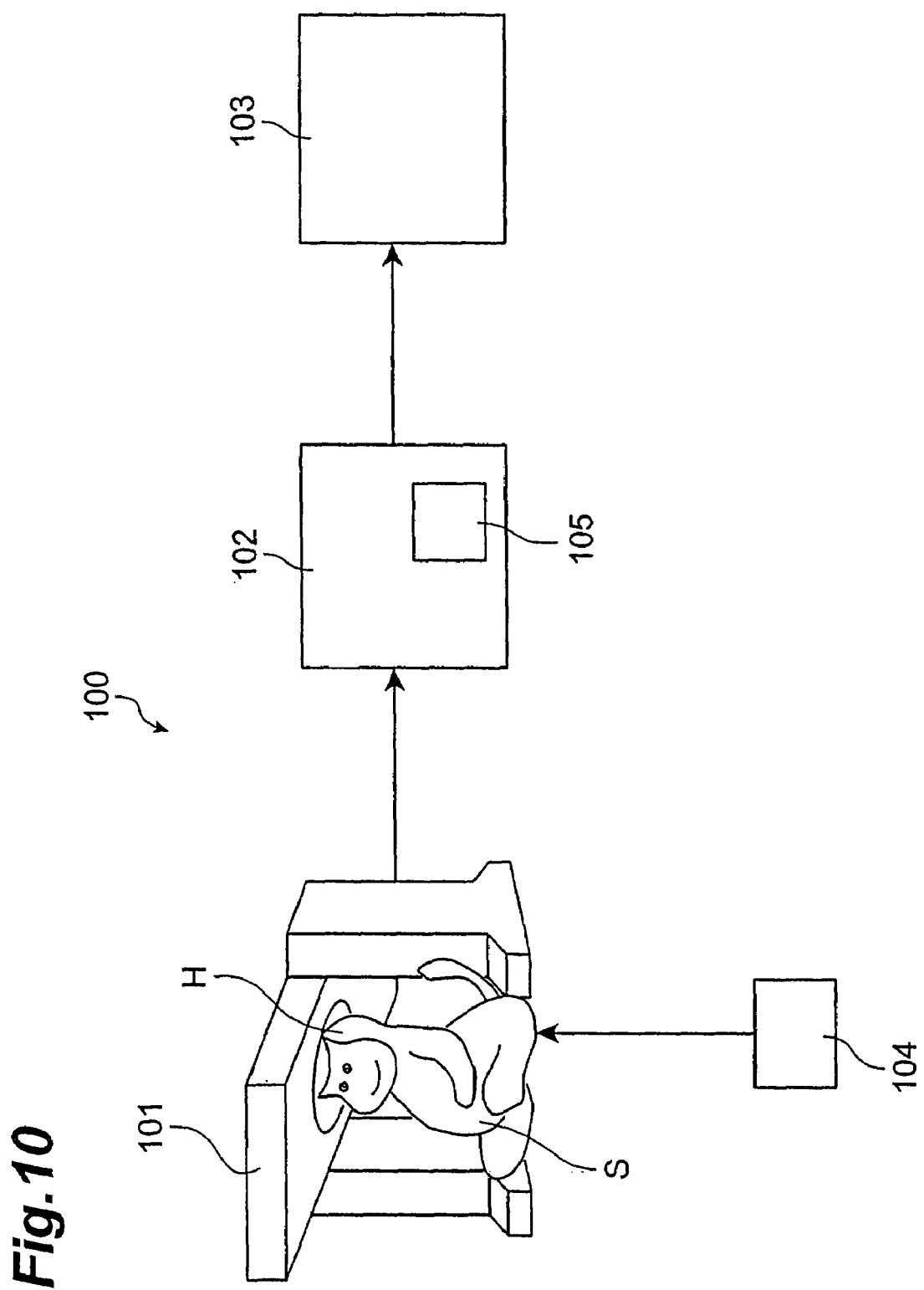

POSITRON EMISSION TOMOGRAPH APPARATUS

TECHNICAL FIELD

The present invention relates to a positron emission tomography apparatus that can be suitably used for example in the evaluation of a drug being tested.

BACKGROUND ART

With a positron emission tomography apparatus (hereinafter referred to as 'PET apparatus'), a positron-emitting labeled substance is administered into a subject, and also coincidence counting is carried out of radiation generated in a measurement-subjected part of the subject accompanying electron-positron pair annihilation, and the spatial distribution of the radiation concentration in the measurement-subjected part is measured and made into an image, and hence for example changes in the amount accumulated of the labeled substance in a specific region of interest of the measurement-subjected part are studied; PET apparatuses are being applied to the evaluation of drugs for Alzheimer-type or vascular-type dementia and so on.

FIG. 10 is a block diagram showing the constitution of a conventional PET apparatus. The PET apparatus 100 has a detection unit 101, a data collection unit 102, an image reconstruction unit 103, and an intravenous injection unit 104. Here, the data collection unit 102 has a frame-dependent histogram count memory 105.

A description will now be given of the operation of this PET apparatus 100. Firstly, a labeled substance T is intravenously injected into a subject S (for example a monkey) using the intravenous injection unit 104. Next, the measurement-subjected part H (for example the head) of the subject S is inserted into a measurement space within the detection unit 101, and then coincidence counting of radiation emitted by the labeled substance T that has reached the head of the subject S is carried out by the detection unit 101, and the coincidence count data is transmitted to the data collection unit 102. In the data collection unit 102, the transmitted coincidence count data is accumulated in the frame-dependent histogram count memory 105, and is summed in accordance with the image frame. The summed data is then sent to the image reconstruction unit 103, and based on this the radiation concentration distribution in the measurement-subjected part H of the subject S is made into an image.

In a drug evaluation test, after the labeled substance T has been administered, the drug being tested Y is administered to the subject S. Then, by carrying out numerical analysis of the radiation concentrations obtained as described above based on physiological constants characteristic of the subject S and so on, the change and so on in the accumulated amount of the labeled substance T in a region of interest of the measurement-subjected part H between before and after the administration of the drug being tested Y is obtained.

DISCLOSURE OF THE INVENTION

With a conventional PET apparatus, in general a method is used in which the labeled substance is injected through a single intravenous injection (the so-called bolus injection method).

However, with this bolus injection method, the S/N ratio drops during the latter half of the measurements due to the half life of the labeled substance, and hence to compensate for this the amount administered of the labeled substance must be set rather high. Consequently, the radiation exposure dose to the subject becomes high, and moreover it is necessary to make the radiation concentration measurement range of the PET apparatus broad so that radiation concentrations from the high radiation concentrations at the start of the measurements to the low radiation concentrations during the latter half of the measurements can be measured.

On the other hand, with conventional PET apparatuses, instead of the bolus injection method, a method has also been used in which the subject is made to continuously inhale a gas containing the labeled substance at a steady rate (the so-called steady gas inhalation method). The aim of this steady gas inhalation method is to make the radiation concentration in the subject be in a steady state.

However, with this steady gas inhalation method, the flow rate and so on of the labeled substance is greatly affected by changes in the physiological state (in particular the respiration rate) of the subject, and hence in actual practice it is difficult to make the radiation concentration in the subject be in a steady state. Many errors are thus contained in the measured radiation concentrations, and the experimental accuracy cannot be guaranteed.

Moreover, with a conventional PET apparatus, to carry out the numerical analysis on the measured data, it is necessary to gain an understanding of the state of the bodily functions (for example the radiation concentration in the blood) of the subject during the experiment. A sample of arterial blood is thus taken from the subject during or after the experiment, this arterial blood is analyzed, and a physiological constant that indicates the state in the subject during the experiment is calculated.

However, taking a sample of arterial blood imposes physical and psychological burdens on the subject, and in addition specialist staff are separately required for taking the blood sample, and furthermore there is a risk of these staff being exposed to radiation from the sampled blood. Moreover, a great deal of staff and expensive equipment (chromatography equipment, auto gamma counter etc.) are required for analyzing the sampled blood.

Furthermore, to carry out numerical analysis using the physiological constant obtained as described above, it is necessary to carry out complex analytical calculations including convolution integrals. Staff and calculating equipment for the numerical analysis are thus separately required, and it may take a long time (e.g. 1 week) until the results are ascertained. In such a case, it is not possible to change the conditions of the next experiment as appropriate based on the results of the immediately preceding experiment, which leads to considerable delays in the progress of the experiments.

In view of the above problems, it is an object of the present invention to provide a positron emission tomography apparatus (PET apparatus) that enables measurements to be carried out easily and precisely, and also enables measurement results to be grasped rapidly and easily.

The positron emission tomography apparatus (PET apparatus) according to the present invention, which is a PET apparatus that administers a positron-emitting labeled substance into a subject, and also carries out coincidence counting of radiation generated in a measurement-subjected part of the subject accompanying electron-positron pair annihilation, and measures the spatial distribution of the radiation concentration in the measurement-subjected part, is characterized by having region-of-interest data extraction means for extracting radiation data for a specified region of interest from out of the radiation data that has been obtained by coincidence counting from the measurement-subjected part, administration condition calculation means for calculating an optimum administration condition for the labeled substance into the subject based on the extracted radiation data for the region of interest, and administration control means for carrying out feedback control of an administration condition for the labeled substance into the subject based on the optimum administration condition.

According to this PET apparatus, radiation data for a region of interest of the measurement-subjected part is extracted for example for each frame, and then an optimum administration condition (e.g. amount administered per unit time) for the labeled substance such that the radiation concentration for the region of interest becomes steady regardless of the physiological state (blood flow rate etc.) of the subject is calculated based on the radiation data, and feedback control is carried out of the amount administered or the like of the labeled substance to the subject in accordance with the optimum administration condition.

If, in this way, feedback control is carried out such that the radiation concentration for the region of interest—not the radiation concentration for the whole of the measurement-subjected part—becomes steady, then there is no longer any need to broaden the radiation concentration measurement range of the PET apparatus. Moreover, it becomes possible to obtain the change in the amount accumulated of the labeled substance in the region of interest between before and after administration of a drug being tested easily and precisely in real time as the amount of change in the radiation concentration. Sampling of arterial blood and complex numerical calculations are thus unnecessary, and hence great cutbacks can be made in the staff, time, analytical equipment and so on required for calculating the experimental results.

BRIEF DESCRIPTION OF THE DRAWINGS

FIG. 10 is a block diagram showing the constitution of a conventional PET apparatus.

BEST MODE FOR CARRYING OUT THE INVENTION

Figure 1:
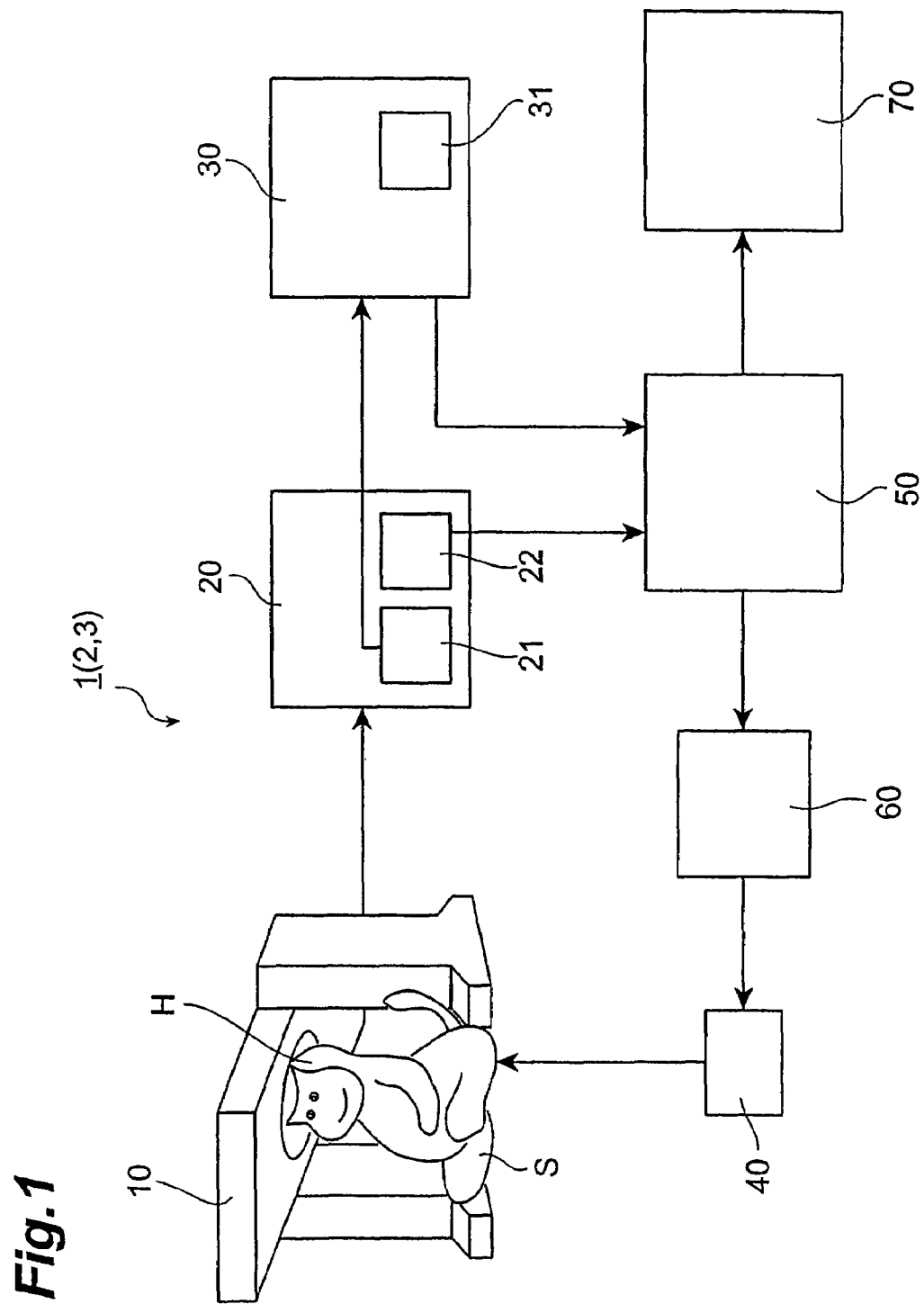
FIG. 1 is a block diagram showing the constitution of a PET apparatus according to a first embodiment.

Following is a detailed description of embodiments of the positron emission tomography apparatus (PET apparatus) according to the present invention, with reference to the accompanying drawings. Note that identical or corresponding elements are represented by the same reference numeral, and redundant repeated description is omitted.

Firstly, a description will be given of a first embodiment of the positron emission tomography apparatus (PET apparatus) according to the present invention. FIG. 1 is a block diagram of the constitution of the PET apparatus 1 according to the first embodiment. As shown in FIG. 1, the PET apparatus 1 comprises a detection unit 10, a data collection unit 20, an image information control unit 30, an intravenous injection unit 40, a calculation processing unit 50, an administration rate control unit 60, and a display unit 70.

The detection unit 10 has contained therein a measurement space into which a measurement-subjected part (for example the head) H of a subject (for example a monkey) S can be placed, and a large number of detectors are arranged in a ring around the central axis. For each of these detectors, the ray-receiving surface faces into the measurement space, and hence the detector detects radiation emitted from the measurement space side. Each of the detectors of the detection unit 10 is connected to the data collection unit 20 by a signal line, and detection signals that depend on the energy of the detected radiation are transmitted from the detectors to the data collection unit 20.

The data collection unit 20 has an imaged-frame-dependent histogram memory 21 and an imaged-frame-independent histogram memory 22. The data collection unit 20 recognizes when a pair of detectors out of the large number of detectors constituting the detection unit 10 have simultaneously detected radiation (energy 511 keV) generated accompanying electron-positron pair annihilation based on the detection signals transmitted from the detection unit 10, and stores the coincidence count data based on the detection signals in the imaged-frame-dependent histogram memory 21 and the imaged-frame-independent histogram memory 22.

The imaged-frame-dependent histogram memory 21 is connected to the image information control unit 30 by a signal line. Moreover, the imaged-frame-independent histogram memory 22 is connected to the calculation processing unit 50 by a signal line. The data accumulated and summed in the imaged-frame-dependent histogram memory 21 is transmitted to the image information control unit 30 in accordance with the imaged frames (time periods that act to delimit the data collection), which are preset.

The image information control unit 30 has an image information memory 31, and information such as a mask image created in advance before commencing measurement is stored in this image information memory 31. The image information control unit 30 is connected to the calculation processing unit 50 by a signal line, and image information and so on stored in the image information memory 31 is transmitted to the calculation processing unit 50 in accordance with the imaged frames and so on.

The intravenous injection unit 40 has an injection needle for carrying out intravenous injection into the subject S, and a pump or the like for injecting the labeled substance T into the subject S. During the measurement period, the injection needle is kept in a state inserted into the subject S, and the labeled substance T is continuously administered using the pump. Moreover, the pump has a structure such that it is possible to change the rate of intravenous injection of the labeled substance T upon receiving control from the administration rate control unit 60, which is the administration control means.

The calculation processing unit 50 extracts radiation data for a specified region of interest K in the measurement-subjected part H based on the coincidence count data transmitted from the imaged-frame-independent histogram memory 22 and the image information transmitted from the image information control unit 30 and so on, and calculates the radiation concentration for the region of interest K and the optimum administration rate (intravenously injected amount per unit time). The calculation processing unit 50 is connected to the administration rate control unit 60 and the display unit 70 by signal lines; the calculated radiation concentration for the region of interest K is transmitted to the display unit 70, and the calculated optimum administration rate is transmitted to the administration rate control unit 60.

The administration rate control unit 60 is connected to the intravenous injection unit 40 by a signal line, and controls the rate of administration by the intravenous injection unit 40 based on the transmitted optimum administration rate information. Moreover, the display unit 70 is a liquid crystal monitor or the like, and displays the transmitted radiation concentration for the region of interest K as a graph or the like.

Figure 2:
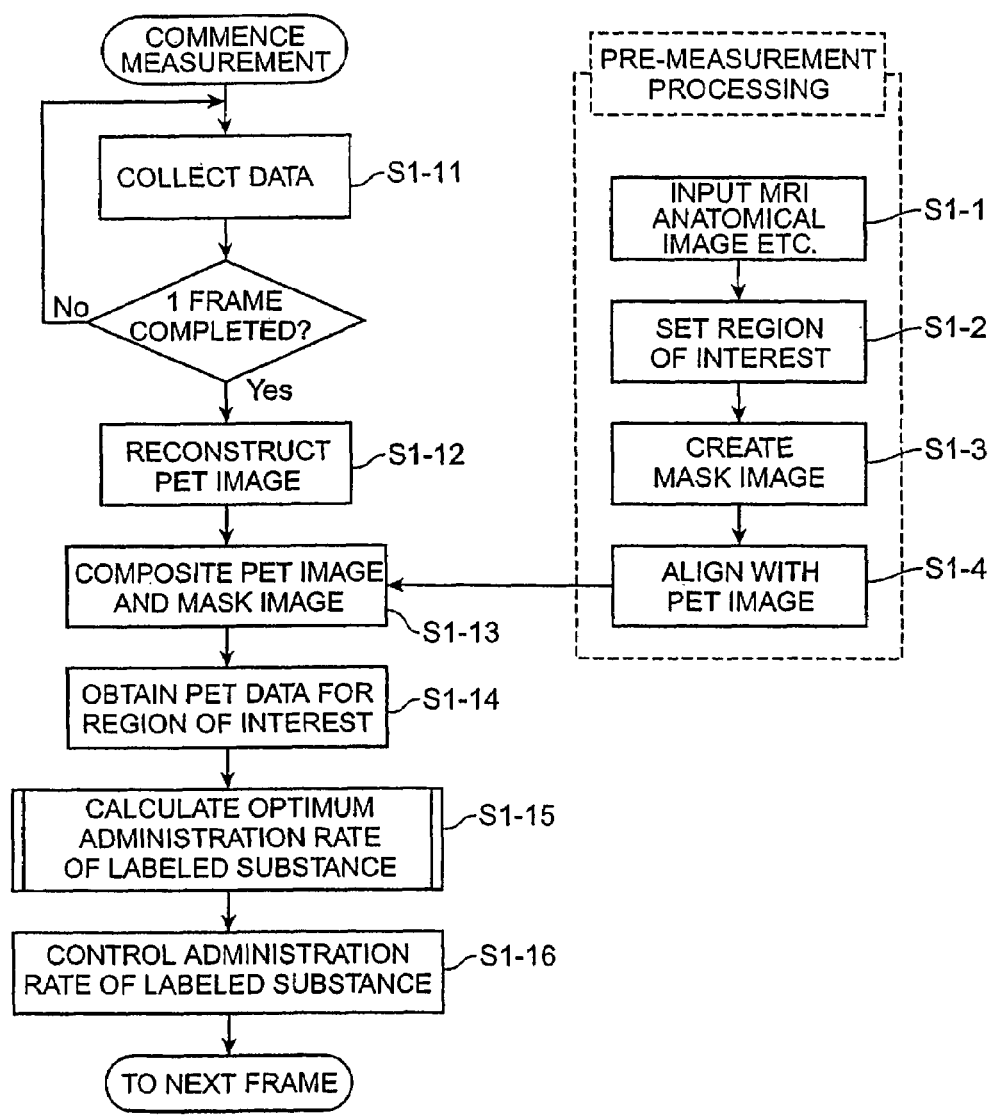
FIG. 2 is a flowchart explaining region-of-interest data extraction processing, administration rate calculation processing and administration rate control processing in the PET apparatus according to the first embodiment.

Next, a description will be given of the operation of the PET apparatus 1 according to the present embodiment with reference to the flowchart shown in FIG. 2, focusing in particular on the region-of-interest data extraction processing, the administration rate calculation processing (administration condition calculation processing) and the administration rate control processing (administration control processing).

Before describing the processing carried out after commencing measurement, a description will be given of processing carried out before commencing measurement. In this pre-measurement processing, firstly an MRI anatomical image or the like of the measurement-subjected part H of the subject S that has been measured in advance is inputted into the image in formation memory 31 of the image information control unit 30 (step 1-1; hereinafter steps are abbreviated to 'S1-1' and so on). Next, the region of interest K is set on this image (S1-2). The region of interest K is a part where the amount accumulated or the like of the labeled substance T changes through the administration of the drug being tested Y, and is selected as appropriate in accordance with the type of the drug being tested Y, the objective and so on.

Next, a mask image that leaves behind only the data for the region of interest K is created based on the set image (S1-3). In this mask image, 1 is set within the region of interest K, and 0 is set in the region other than the region of interest K. After the mask image has been created, alignment of the mask image and the PET image is carried out (S1-4).

After the pre-measurement processing has been carried out as described above, measurement is commenced. The measurement-subjected part H of the subject S is inserted into the measurement space of the detection unit 10, and administration of the labeled substance T (for example a compound containing positron-emitting $^{15}O$ or the like) into the subject S is commenced. Coincidence counting of the radiation generated from the measurement-subjected part H due to electron-positron pair annihilation is then carried out, and the coincidence count data is collected in the imaged-frame-dependent histogram memory 21 and the imaged-frame-independent histogram memory 22 (S1-11). The coincidence count data is collected repeatedly until one frame has been completed, with the coincidence count data being accumulated in the imaged-frame-dependent histogram memory 21 and the imaged-frame-independent histogram memory 22.

Figure 3:
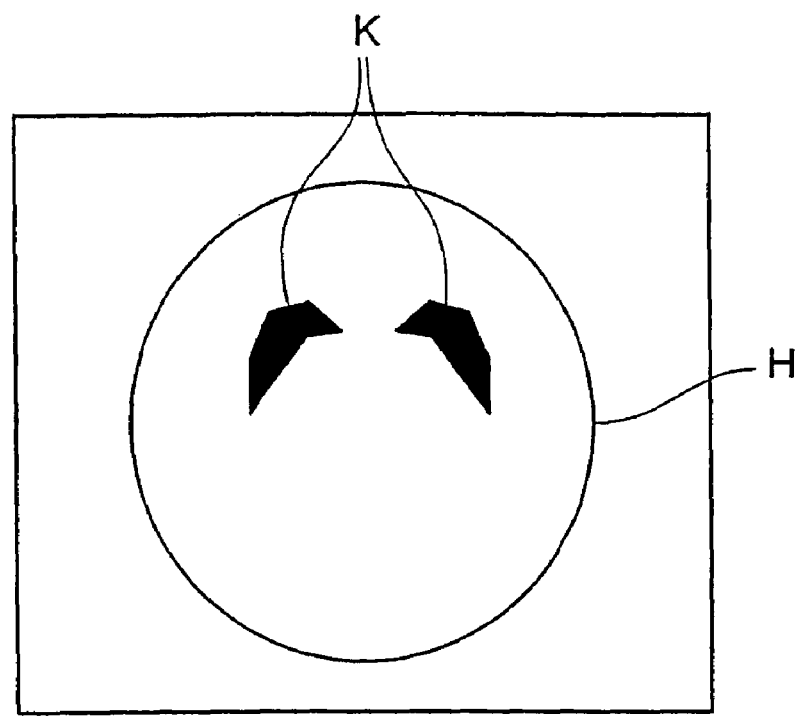
FIG. 3 is a schematic drawing for explaining extraction of radiation data for the region of interest in the PET apparatus according to the first embodiment.

Once the frame has been completed, the summed coincidence count data is transmitted to the calculation processing unit 50, and reconstruction of the PET image (radiation data image) of the measurement-subjected part H is carried out based on the coincidence count data (S1-12). At this time, the pre-aligned mask image is transmitted from the image information control unit 30 to the calculation processing unit 50. The reconstructed PET image and the mask image are then composited in the calculation processing unit 50 (S1-13). Through this composition, the PET image for the region of interest K (i.e. an image that shows the radiation concentration distribution within the region of interest) is extracted, for example as shown in FIG. 3.

Next, in the calculation processing unit 50, PET data (radiation concentration data) for the region of interest K is obtained based on the extracted PET image for the region of interest K (S1-14). This PET data for the region of interest K is transmitted to the display unit 70, and is displayed as a graph or the like. Moreover, in the calculation processing unit 50, the optimum administration rate such that the radiation concentration for the region of interest K will be steady is calculated based on the PET data for the region of interest K (S1-15).

Figure 4:
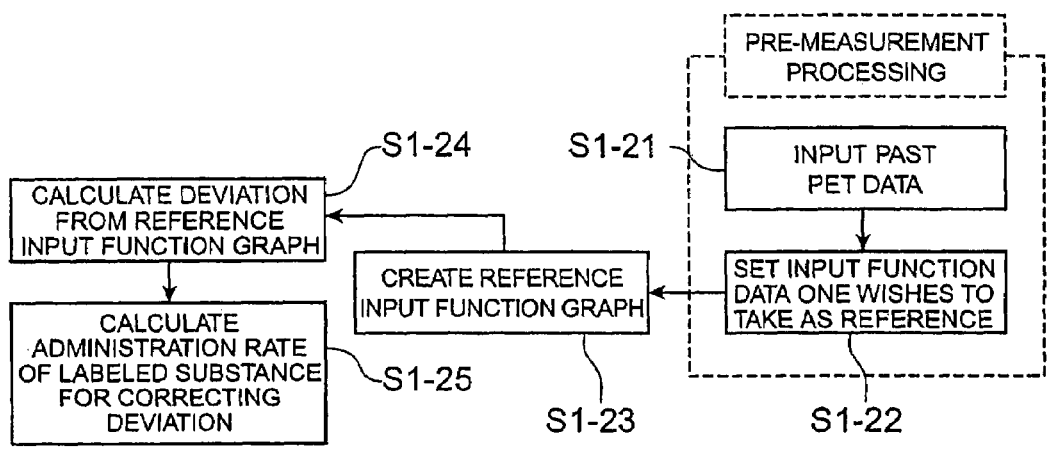
FIG. 4 is a detailed flowchart explaining the administration rate calculation processing in the PET apparatus according to the first embodiment.

Here, the processing to calculate the optimum administration rate (optimum administration condition) will be described in detail with reference to the flowchart shown in FIG. 4. As pre-processing when carrying out this calculation processing, past PET data is inputted into the image information memory 31 of the image information control unit 30 in advance (S1-21). Out of the inputted PET data, input function data that one wishes to take as a reference is then preset (S1-22), and a reference input function graph is created based on this reference input function data (S1-23).

After the PET data for the region of interest K has been calculated in S1-14, the deviation between the reference input function graph that has been created in advance and the graph from the calculated PET data is calculated (S1-24). The optimum administration rate of the labeled substance T for correcting this deviation is then calculated (S1-25). Note that the graph from the PET data obtained for this frame may be substituted for the preset reference input function graph, and used as the reference input function graph for the next frame.

Afterwards, information on the calculated optimum administration rate is transmitted to the administration rate control unit 60, and the administration rate control unit 60 carries out feedback control such that the administration rate (administration condition) of the labeled substance T in the intravenous injection unit 40 becomes the optimum administration rate (S1-16). Once the above sequence of processing has been completed, the measurement progresses to the next frame. During the measurement for the next frame, the intravenous injection unit 40 administers the labeled substance T to the subject S at the calculated optimum administration rate.

The above processing is repeated, progressing from frame to frame. Because feedback control of the administration rate is carried out for each frame, as the frames are progressed through, the radiation concentration generated from the region of interest K becomes steady. The drug being tested Y is administered to the subject S after the radiation concentration generated from the region of interest K has reached a steady state. The drug being tested Y is then evaluated by observing the change in the radiation concentration generated from the region of interest K (i.e. the change in the amount accumulated of the labeled substance T).

Figure 5:
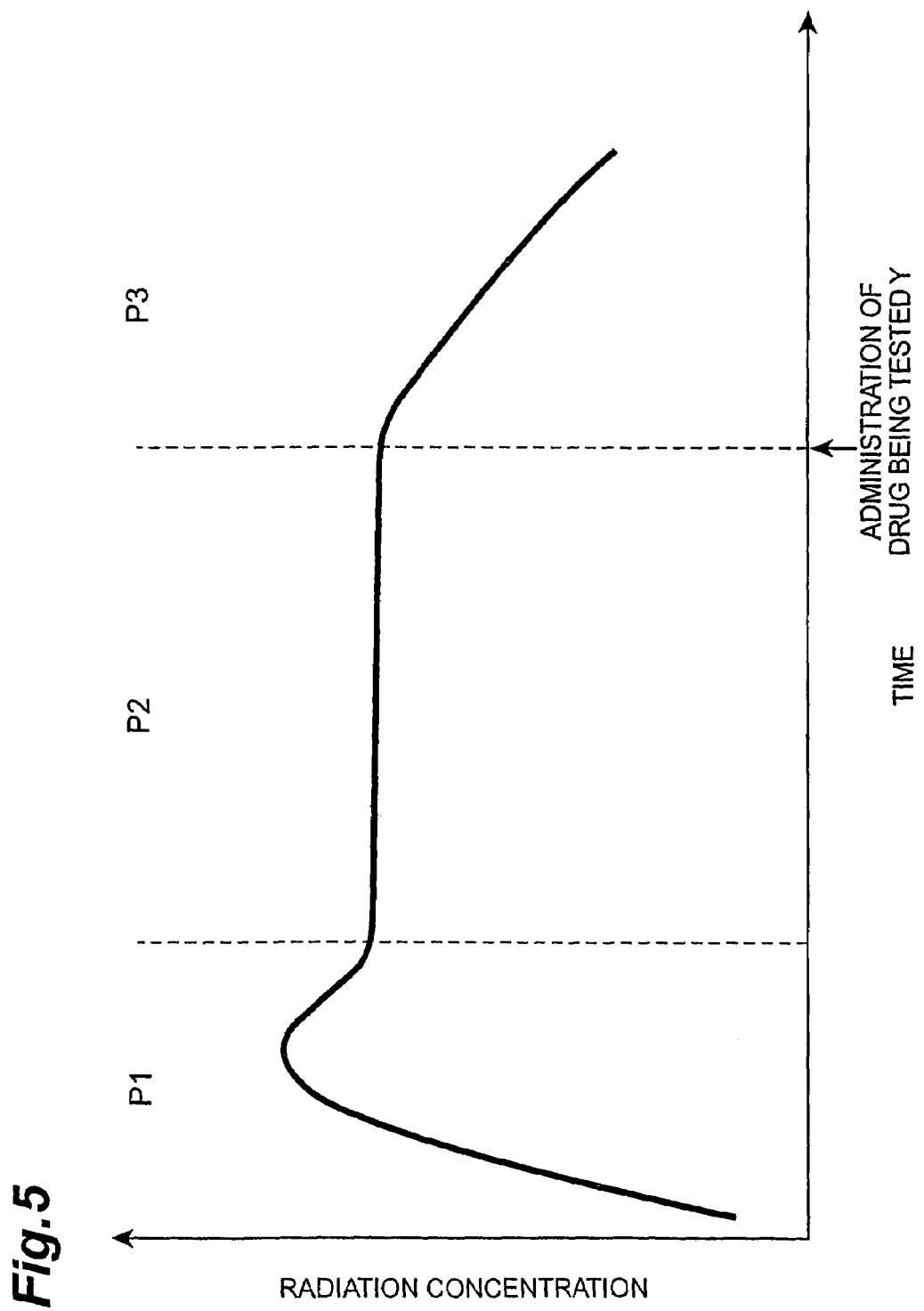
FIG. 5 is a graph showing the changes over time in the radiation concentration for the region of interest in the case of the PET apparatus according to the first embodiment.

FIG. 5 is a graph showing the changes over time in the radiation concentration for the region of interest in the case of the PET apparatus according to the present embodiment; such a graph can be visually checked in real time on the display unit 70. As shown in FIG. 5, the changes over time in the radiation concentration generated from the region of interest K can broadly be divided into 3 periods.

The first period P1 is a stage when the radiation concentration for the region of interest K is still not stable, depending on the blood flow rate and so on. The second period P2 is a stage when, due to feedback control of the administration rate of the labeled substance T having been carried out, the radiation concentration for the region of interest K has reached a steady state. The third period P3 is a stage when changes have arisen in the radiation concentration for the region of interest K, which had been in a steady state, due to administration of the drug being tested Y. In the present embodiment, the effect of the drug being tested Y is evaluated by studying the changes in the radiation concentration for the region of interest K during the period P3.

According to the PET apparatus 1 of the present embodiment, for each frame, after the coincidence count data for the region of interest of the measurement-subjected part has been extracted, the optimum administration rate of the labeled substance such that the radiation concentration for the region of interest K will be steady regardless of the physiological state (blood flow rate etc.) of the subject S is calculated as an optimum administration condition, this being based on the radiation concentration data for the region of interest K obtained from the coincidence count data. Feedback control of the administration rate of the labeled substance T to the subject S is then carried out based on the calculated optimum administration rate.

If, in this way, feedback control is carried out such that the radiation concentration for the region of interest K—not the radiation concentration for the whole of the measurement-subjected part H—becomes steady, then there is no longer any need to broaden the radiation concentration measurement range. Moreover, it becomes possible to obtain the change in the amount accumulated of the labeled substance T in the region of interest K between before and after administration of the drug being tested Y easily and precisely in real time as the amount of change in the radiation concentration. Sampling of arterial blood and complex numerical analysis are thus unnecessary, and hence great cutbacks can be made in the staff, time, analytical equipment and so on required for calculating the experimental results.

Moreover, with the PET apparatus 1 according to the present embodiment, the extracted radiation concentration data is displayed in real time on the display unit 70 as a graph or the like. It thus becomes possible to visually check changes and so on in the radiation concentration for the region of interest K easily in real time, and hence the measurement results and so on can be judged rapidly.

Moreover, with the PET apparatus 1 according to the present embodiment, by extracting the radiation data for the region of interest as an image, the accuracy of the extraction can be raised, and in addition the extraction can be carried out as radiation concentrations, not as coincidence count data.

Furthermore, with the PET apparatus 1 according to the present embodiment, a reference input function graph is created in advance, and the administration rate of the labeled substance T such as to correct the deviation from the reference input function graph is calculated. There is thus no longer any need to carry out complex calculations or analysis not only in the case that measurements are carried out a plurality of times on the same subject, but even in the case that measurements are carried out on a plurality of subjects (i.e. subjects having different physiological constants).

Figure 6:
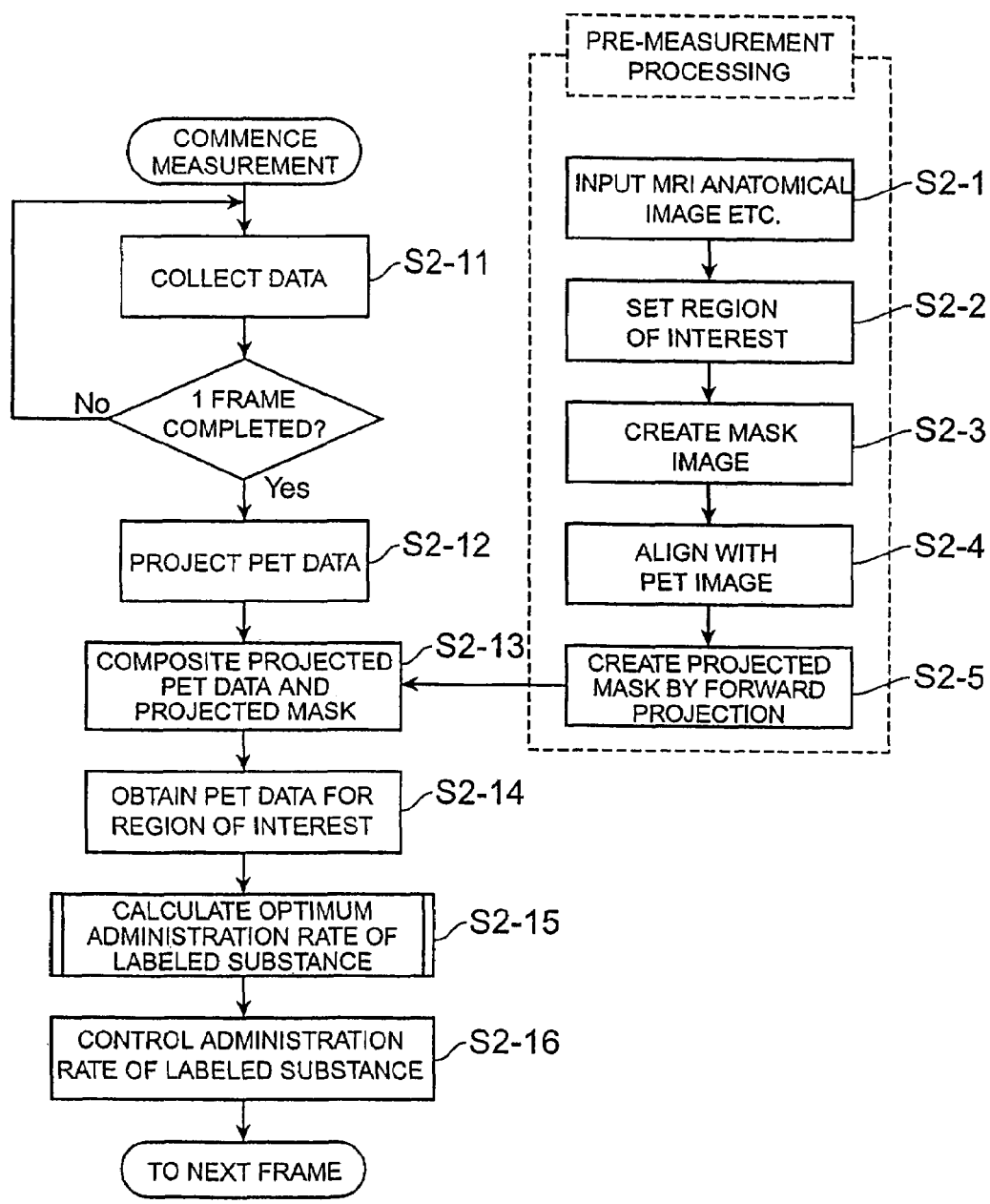
FIG. 6 is a flowchart explaining region-of-interest data extraction processing and administration rate control processing in a PET apparatus according to a second embodiment.

Next, a description will be given of a second embodiment of the positron emission tomography apparatus (PET apparatus) according to the present invention. The constitution of the PET apparatus 2 according to the second embodiment is very similar to that of the first embodiment, and hence here a description will be given of the operation of the PET apparatus 2 with reference to the flowchart shown in FIG. 6, focusing in particular on the region-of-interest data extraction processing, the administration rate calculation processing and the administration rate control processing.

Before describing the processing carried out after commencing measurement, a description will be given of processing carried out before commencing measurement. In this pre-measurement processing, as in the first embodiment, an MRI anatomical image or the like of the measurement-subjected part H of the subject S that has been measured in advance is inputted into the image information memory 31 of the image information control unit 30 (S2-1), and then the region of interest K is set on this image (S2-2).

Next, a mask image that leaves behind only the data for the region of interest K is created based on the set image (S2-3), and then alignment of the mask image and the PET image is carried out (S2-4). After this, in the present embodiment, forward projection of the mask image onto projection data is carried out, thus creating a projected mask (S2-5).

After the pre-measurement processing has been carried out as described above, measurement is commenced. The measurement-subjected part H of the subject S is inserted into the measurement space of the detection unit 10, and administration of the labeled substance T into the subject S is commenced. Coincidence counting of the radiation generated from the measurement-subjected part is then carried out, and the coincidence count data is collected in the imaged-frame-dependent histogram memory 21 and the imaged-frame-independent histogram memory 22 (S2-11). The coincidence count data is collected repeatedly until one frame has been completed, with the coincidence count data being accumulated in the imaged-frame-dependent histogram memory 21 and the imaged-frame-independent histogram memory 22.

Figure 7:
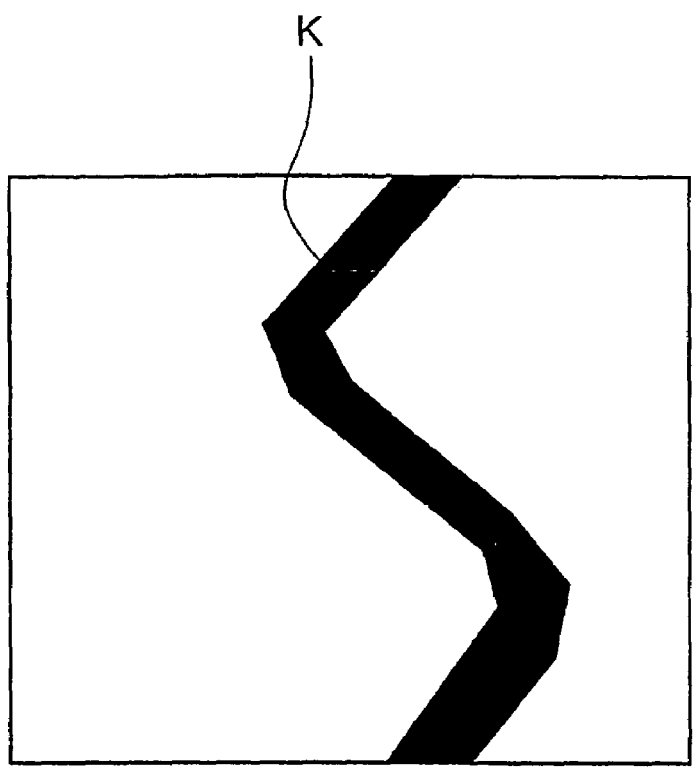
FIG. 7 is a schematic drawing for explaining extraction of radiation data for the region of interest in the PET apparatus according to the second embodiment.

Once the frame has been completed, the summed coincidence count data is transmitted to the calculation processing unit 50, and forward projection of this data onto the projection data is carried out (S2-12). At this time, the pre-aligned projected mask is transmitted onto the projection data in the calculation processing unit 50 from the image information control unit 30. The projected PET data (projected radiation data) and the projected mask are then composited in the calculation processing unit 50 (S2-13) Through this composition, the projected PET data for the region of interest K is extracted, for example as shown in FIG. 7.

Next, in the calculation processing unit 50, PET data for the region of interest K is obtained based on the extracted projected PET data for the region of interest K (S2-14). This PET data for the region of interest K is transmitted to the display unit 70, and is displayed as a graph or the like.

Moreover, in the calculation processing unit 50, as in the first embodiment, the optimum administration rate such that the radiation concentration for the region of interest K will be steady is calculated based on the PET data for the region of interest K (S2-15).

Afterwards, information on the calculated optimum administration rate is transmitted to the administration rate control unit 60, and the administration rate control unit 60 carries out feedback control such that the administration rate of the labeled substance T in the intravenous injection unit 40 becomes the optimum administration rate (S2-16). Once the above sequence of processing has been completed, the measurement progresses to the next frame. During the measurement for the next frame, the intravenous injection unit 40 administers the labeled substance T into the subject S at the calculated optimum administration rate.

According to the PET apparatus 2 of the present embodiment, because compositing is carried out of the projected radiation data for the region of interest K and the projected mask on the projection data, it becomes possible to improve the temporal resolution.

Figure 8:
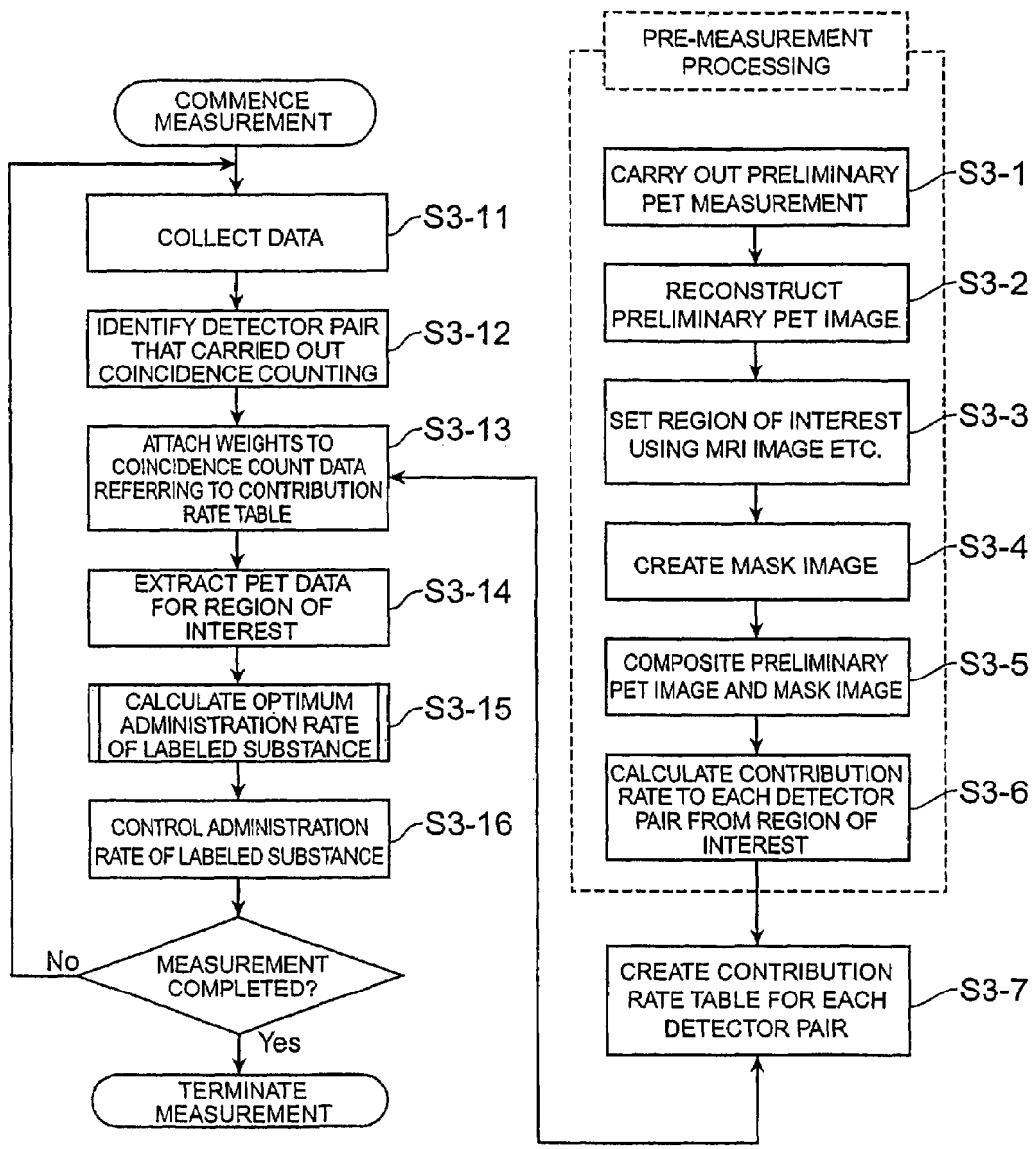
FIG. 8 is a flowchart explaining region-of-interest data extraction processing and administration rate control processing in a PET apparatus according to a third embodiment.

Finally, a description will be given of a third embodiment of the positron emission tomography apparatus (PET apparatus) according to the present invention. The constitution of the PET apparatus 3 according to the third embodiment is very similar to that of the first embodiment, and hence here a description will be given of the operation of the PET apparatus 3 with reference to the flowchart shown in FIG. 8, focusing in particular on the region-of-interest data extraction processing, the administration rate calculation processing and the administration rate control processing.

Before describing the processing carried out after commencing measurement, a description will be given of processing carried out before commencing measurement. In this pre-measurement processing, PET measurement is carried out in advance on the measurement-subjected part H of the subject S (S3-1). A PET image is then reconstructed based on the PET data obtained through this preliminary PET measurement (S3-2).

Moreover, as in the first embodiment, an MRI anatomical image or the like of the measurement-subjected part H of the subject S that has been measured in advance is inputted into the image information memory 31 of the image information control unit 30, and the region of interest K is set on this image (S3-3). Next, a mask image that leaves behind only the data for the region of interest K is created based on the set image (S3-4), and then the mask image and the preliminary PET image are composited (S3-5).

Figure 9:
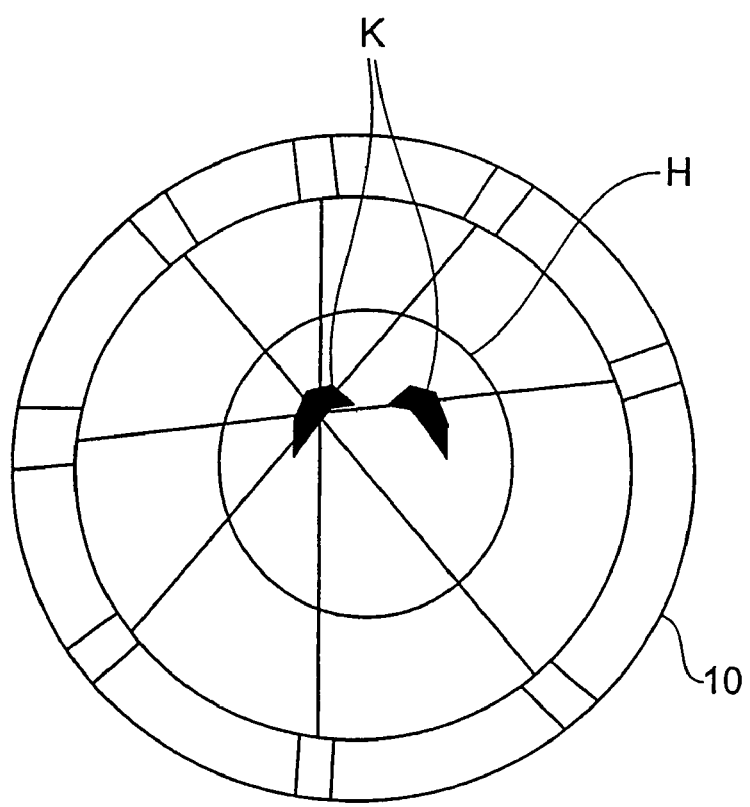
FIG. 9 is a schematic drawing for explaining the calculation of detector pair contribution rates in the PET apparatus according to the third embodiment.

Next, based on the composited image, the contribution rate to each detector pair from the region of interest K is calculated (S3-6). This contribution rate is the proportion contributed by the radiation generated from the region of interest K out of the coincidence count value detected by the detector pair in question; for example, in the case shown in FIG. 9, a value between 0 and 1 is set for each detector pair based for example on the distance for which the line segment joining the pair of detectors cuts through the region of interest K or on the radiation concentration distribution obtained from the preliminary PET image. A contribution rate table in which are collated the contribution rates for the respective detector pairs is then created (S3-7).

After the pre-measurement processing has been carried out as described above, measurement is commenced. The measurement-subjected part H of the subject S is inserted into the measurement space of the detection unit 10, and administration of the labeled substance T into the subject S is commenced. Coincidence counting of the radiation generated from the measurement-subjected part is then carried out (S3-11). In the present embodiment, the coincidence count data obtained is transmitted to the calculation processing unit 50 not frame by frame but rather in time series fashion. In the calculation processing unit 50, the detector pairs that detected the coincidence count data are identified (S3-12).

At this time, the contribution rate table for the detector pairs which has been created in advance is transmitted to the calculation processing unit 50, and based on this the coincidence count data is subjected to weighting processing (S3-13). For example, in the case that the detection was by a detector pair for which the contribution rate is 0.7 (70%), a coincidence count of 1 is reduced to 0.7. Note that, at this time, a contribution rate table including the coincidence count data obtained may be newly created, with this being used when the next coincidence count data is subjected to the weighting processing.

Next, in the calculation processing unit 50, PET data for the region of interest K is extracted (S3-14) based on the coincidence count data that has been weighted as described above. This PET data for the region of interest K is transmitted to the display unit 70, and is displayed as a graph or the like. Moreover, in the calculation processing unit 50, as in the first embodiment, the optimum administration rate such that the radiation concentration for the region of interest K will be steady is calculated based on the PET data for the region of interest K (S3-15).

Afterwards, information relating on the calculated optimum administration rate is transmitted to the administration rate control unit 60, and the administration rate control unit 60 carries out feedback control such that the administration rate of the labeled substance T in the intravenous injection unit 40 becomes the optimum administration rate (S2-16). In the present embodiment, the PET imaging progresses to the next frame once one frame has been completed. However, the calculation and control of the optimum administration rate is carried out as appropriate independently of the frame, and hence the intravenous injection unit 40 administers the labeled substance T to the subject S at the optimum administration rate for the time in question.

According to the PET apparatus 3 of the present embodiment, because time-series-type data based on each of the detector pairs is used, it becomes possible to extract radiation data for the region of interest K with an extremely high temporal resolution.

The positron emission tomography apparatus (PET apparatus) according to the present invention is not limited to the above embodiments, with it being possible to adopt various modifications in accordance with other conditions and so on. For example, in the above embodiments, the functions of the region-of-interest data extraction means for carrying out processing to extract the radiation data for the region of interest K, and the functions of the administration condition calculation means for carrying out processing to calculate the optimum administration condition are realized using a single calculation processing unit 50. However, a constitution is also possible in which these pieces of processing are carried out by processing units provided separately via signal lines, i.e. by a region-of-interest data extraction processing unit and an administration condition calculation processing unit respectively.

INDUSTRIAL APLICABLILITY

As described above, the positron emission tomography apparatus (PET apparatus) according to the present invention can be used as a positron emission tomography apparatus that enables measurements to be carried out easily and precisely, and also enables measurement results to be grasped rapidly and easily.

That is, it is no longer necessary to broaden the radiation concentration measurement range of the PET apparatus, and moreover it becomes possible to obtain the amount of change and so on in the radiation concentration for a region of interest between before and after administration of a drug being tested easily and precisely in real time. Sampling of arterial blood and complex numerical analysis are thus unnecessary, and hence great cutbacks can be made in the staff, time, analytical equipment and so on required for calculating the experimental results.

The invention claimed is:

1. A positron emission tomography apparatus, which administers a positron-emitting labeled substance into a subject, and also carries out coincidence counting of radiation generated in a measurement-subjected part of said subject accompanying electron-positron pair annihilation, and measures the spatial distribution of the radiation concentration in said measurement-subjected part, comprising:
   region-of-interest data extraction means for extracting radiation data for a specified region of interest, which is a region selected in said measurement-subjected part, from out of the radiation data that has been obtained by coincidence counting from said measurement-subjected part;
   administration condition calculation means for calculating an optimum administration condition for said labeled substance into said subject based on the extracted radiation data for said region of interest; and
   administration control means for carrying out feedback control of an administration condition for said labeled substance into said subject based on said optimum administration condition.

2. The position emission tomography apparatus according to claim 1, further comprising region-of-interest data display means capable of instant image display of the extracted radiation data for said region of interest.

3. The positron emission tomography apparatus according to claim 1, wherein said region-of-interest data extraction means sets said region of interest on an image in which positional information on said measurement-subjected parted is displayed;
   creates a radiation data image by carrying out image reconstruction of the radiation data that has been obtained by coincidence counting from said measurement-subjected part, and a mask image in which radiation data for a region other than said region of interest is eliminated from said image,
   and extracts radiation data for said region of interest by compositing said radiation data image and said mask image.

4. The positron emission tomography apparatus according to claim 1, wherein said region-of-interest data extraction means sets said region of interest on an image in which positional information on said measurement-subjected part is displayed,
   creates a mask image in which radiation data for a region other than said region of interest is eliminated from said image,
   creates projected radiation data by projecting the radiation data that has been obtained by coincidence counting from said measurement-subjected part onto projection data, and a projected mask by projecting said mask image onto said projection data,
   and extracts radiation data for said region of interest by compositing said projected radiation data and said projected mask.

5. The positron emission tomography apparatus according to claim 1, wherein said region-of-interest data extraction means sets said region of interest on an image in which positional information on said measurement-subjected part is displayed,
   carries out weighting of a plurality of pieces of coincidence count data detected from said measurement-subjected part based on the positional relationship between said region of interest and a line segment joining a detector pair that obtained each piece of said coincidence count data,
   and extracts radiation data for said region of interest based on the said weighting.

6. The positron emission tomography apparatus according to claim 1, wherein said administration control means carries out, for each imaged frame, feedback control of the administration condition for said labeled substance into said subject based on said optimum administration condition.

* * * * *